United States Patent
Tash

(10) Patent No.: US 6,216,283 B1
(45) Date of Patent: Apr. 17, 2001

(54) ELEPHANT NOSE PLUNGER

(76) Inventor: George Tash, 5777 Balcom Canyon Rd., Somis, CA (US) 93066

( * ) Notice: Subject to any disclaimer, the term of this patent is extended or adjusted under 35 U.S.C. 154(b) by 0 days.

(21) Appl. No.: 09/310,637

(22) Filed: May 12, 1999

Related U.S. Application Data

(60) Provisional application No. 60/097,004, filed on Aug. 18, 1998.

(51) Int. Cl.$^7$ ........................................ E03D 9/00
(52) U.S. Cl. ........................ 4/255.11; 4/255.01; 4/255.05; 4/255.08
(58) Field of Search ............................. 4/255.01, 255.12; D32/35

(56) References Cited

U.S. PATENT DOCUMENTS

| | | | |
|---|---|---|---|
| D. 46,996 | 2/1915 | Howell | D32/35 |
| D. 155,489 | 10/1949 | Mesquita | D32/35 |
| D. 159,726 | 8/1950 | Grosvold | D32/35 |
| D. 202,979 | 11/1965 | Krusche | D32/35 |
| D. 292,631 | 11/1987 | Tash | D32/35 |
| D. 364,251 | 11/1995 | Novak | D32/35 |
| D. 381,146 | 7/1997 | Tash | D32/35 |
| D. 381,147 | 7/1997 | Tash | D32/35 |
| D. 385,073 | 10/1997 | Tash | D32/35 |
| 1,180,323 | 4/1916 | Schuh | 4/255.11 |
| 1,644,436 * | 10/1927 | Locke | 4/255.11 |
| 1,852,071 | 4/1932 | Becker | 4/255.11 |
| 2,126,689 | 8/1938 | Pouliot | 4/255 |
| 2,195,830 | 4/1940 | Schubring | 4/255 |
| 2,296,149 * | 9/1942 | De France | 4/255.11 |
| 2,473,452 | 6/1949 | Scott | 15/104.3 |
| 2,844,826 | 7/1958 | Cheiten | 4/257 |
| 3,336,604 | 8/1967 | Lacey et al. | 4/255 |
| 3,644,943 | 2/1972 | Leonardo et al. | 4/255 |
| 3,937,404 | 2/1976 | Johnson | 239/567 |
| 3,994,032 | 11/1976 | Spickofsky | 4/255 |
| 4,539,985 | 9/1985 | Magrath | 128/205.1 |
| 4,745,641 | 5/1988 | Tash | 4/255 |
| 5,927,492 * | 7/1999 | Moore | 4/255.11 |

* cited by examiner

Primary Examiner—Henry J. Recla
Assistant Examiner—Tuan Nguyen
(74) Attorney, Agent, or Firm—Lyon, Harr & DeFrank, LLP; Richard T. Lyon; Katrina A. Lyon

(57) ABSTRACT

A toilet bowl plunger for use with a new narrow throat 1.6 gallon toilet that can be used equally well with older toilets. The head portion of the plunger is a pleated bellows consisting of two sections, a conically tapering section and a constant average diameter section. The conically tapering section has larger diameter at the rear end of the head and tapers down to a narrower diameter in a direction away from the rear end of the head. The bellows then continues into the constant diameter section in a direction away from the rear end and towards the front end of the head. The constant diameter section resembles an elephant-like trunk or nose. When inserted into the toilet bowl, the constant diameter section of the bellows head penetrates into the throat, while a forward end of the tapered section seats over the outer perimeter of the mouth of the throat. The constant diameter section or nose of the head curves to follow the path of the throat. The stiffer forward portion of the nose follows the throat without compressing or jamming. As pressure is applied downward on the handle, the tapered section of the bellows compresses against the mouth of the throat forming a seal. As a result, pressure is generated in the throat by the compression of the bellows and/or water/air is directed through the nose section that is curved to follow the path of the throat and thus directed in a direction towards any obstruction in the throat for effectively dislodging the obstruction.

19 Claims, 3 Drawing Sheets

ELEPHANT NOSE PLUNGER

This application claims priority under 35 U.S.C. Section 119(e)(1) of provisional application Ser. No. 60/097,009, filed Aug. 18, 1998.

BACKGROUND OF THE INVENTION

Technical Field

This invention relates to an improved toilet bowl plunger for use with a new narrow throat 1.6 gallon toilet. However, the plunger of the present invention can be used equally well with conventional or standard toilets.

Background Art

There are various problems associated with plunging a clogged toilet. Some of these problems are related to the toilet configuration, while other problems are related to the design of the plunger itself.

By way of background, toilet drains are usually unclogged by using a toilet plunger comprised of a large deformable plunger cup mounted on the end of an elongated handle shaft. During the plunging operation, the plunger cup is held over the mouth of the toilet bowl drain while the plunger handle is reciprocated in an upward and downward motion that alternately contracts and enlarges the space within the cup. Preferred plunging action creates an alternating pressure and suction force in the drain passage that is often sufficient to dislodge an obstruction.

Recently toilets have been redesigned to conserve water. The newer toilets, as compared to older models, have a substantially reduced water flow (approximately 1.6 gallons per flush) and smaller waste drain passages than their older counterparts Since the waste drain passages, or throats, of the newer toilets are narrower, these toilets are more prone to clogging. As shown in FIG. 1, the new 1.6 gallon toilets 10 have a bowl 12 which drains through a relatively narrow throat 14. Conventional plungers are typically too wide to fit into the narrow throat of the new toilet. As such, they do not seal the throat opening. Consequently, conventional plungers are unable to provide the appropriate pressure or suction for the purpose of dislodging any obstruction blocking the throat. As a result, the user must have different plungers on hand for use with new and old toilets.

Another problem related to the configuration of the newer toilets, as can be determined by looking at FIG. 1, is that while the older toilets have a waste drain passage located at the bottom of the toilet bowl, the newer toilets have a waste drain passage or throat that is vertically located in relation to the toilet bowl. The fact that the drain passage or throat is vertical in relation to the bowl makes it practically impossible to use a standard plunger to plunge the toilet since the position of the throat makes it difficult to get the conventional plunger head to seal around the throat.

In addition to problems related to the newer toilet designs, there are two common problems that frequently occur during plunging operations which are related to the design of the common toilet plunger. These are "splash back" and "spillover". First of all, the pressure and suction generated during plunging often causes water to spray out from any gaps between the plunger cup and bowl surface with great force, and then splash up and outside of the toilet bowl onto the plunger operator and onto nearby walls and floors. This phenomenon is called "splash back". Additionally, many times when a toilet is clogged, the water and sewage in the toilet tend to fill the toilet to the brim. Hence, when the toilet plunger head is inserted into the toilet, the displacement of the toilet plunger head causes the toilet water and sewage to spill over the sides of the toilet. This phenomenon is called "spill over".

Therefore, in order to overcome the limitations of prior toilet plungers, what is needed is a toilet plunger that can be used with the newer 1.6 gallon toilets. This plunger should be able to effectively plunge toilets that have throat or waste drain passages that are difficult to access, including those where the throat is generally perpendicular in relation to the toilet bowl. However, this improved plunger should also be compatible with the older toilet models. Furthermore, this plunger should minimize spillage and splash back problems during plunging operations. The plunger should also be simple, capable of being easily fabricated and used, and be inexpensive and durable.

SUMMARY

The toilet drain plunger of the present invention satisfies all of the foregoing needs. This plunger can be used with the new narrow throat 1.6 gallon toilets, even those with a vertically oriented drain hole, but can equally well be used with older toilets of various configurations. The design of the plunger embodied in the present invention is such that plunger head displacement is minimized so that the problem of spill over is lessened. Additionally, the plunger design minimizes splash-back as well. Furthermore, the plunger can be easily and inexpensively molded, preferably of durable rubber or plastic. The plunger is also easy to use.

The plunger of the present invention has a handle and a head. In a preferred embodiment, the head portion of the plunger of the present invention consists of two sections, a first section that is a pleated bellows and a second section extending from the first section which is sized to interface with the throat of a toilet. The first bellows section has a larger diameter at the rear end of the head and tapers down to a narrower diameter in a direction away from the rear end of the head. The bellows section then continues to the second section of the head in a direction away from the rear end and towards the front end of the head. The second section of the head preferably has a pleated-rib structure with a constant average diameter, and resembles an elephant-like trunk or nose. The second section of the plunger's head also preferably has two annular semi-circular shell sections abutting each other at the distal end of the second section, which interface with the throat of the toilet and cause the front most end of the plunger head to be stiff. A narrow lip section extends from the front end of the most forward annular semicircular shell toward the forward end of the head.

When inserted into the toilet bowl, the second, constant diameter section of the head penetrates into the toilet's throat, while the forward end of the first, larger diametered, bellows section of the head seats over the outer perimeter of the mouth of the throat. The second, constant diameter section of the head flexes and bends to follow the path of the throat due to the pleated-rib design of the plunger. Thus, it can readily follow the path of the throat and access vertical throats and other throats that are in hard to reach places. The stiffer forward portion of the second section of the plunger's head follows the throat without compressing or jamming. As pressure is applied downward on the handle, the first bellows section of the head compresses against the mouth of the toilet throat forming a seal. As a result, the pressure generated by the compression of the bellows is directed through the second constant diameter section of the head, along the path of the throat and towards any obstruction. This tends to effectively dislodge the obstruction.

DESCRIPTION OF THE DRAWINGS

The specific features, aspects, and advantages of the present invention will become better understood with regard to the following description, appended claims and accompanying drawings where:

DETAILED DESCRIPTION OF THE PREFERRED EMBODIMENTS

In the following description of the preferred embodiments of the present invention, reference is made to the accompanying drawings, which form a part hereof, and which is shown by way of illustration of specific embodiments in which the invention may be practiced. It is understood that other embodiments may be utilized and structural changes may be made without departing from the scope of the present invention.

Figure 1:
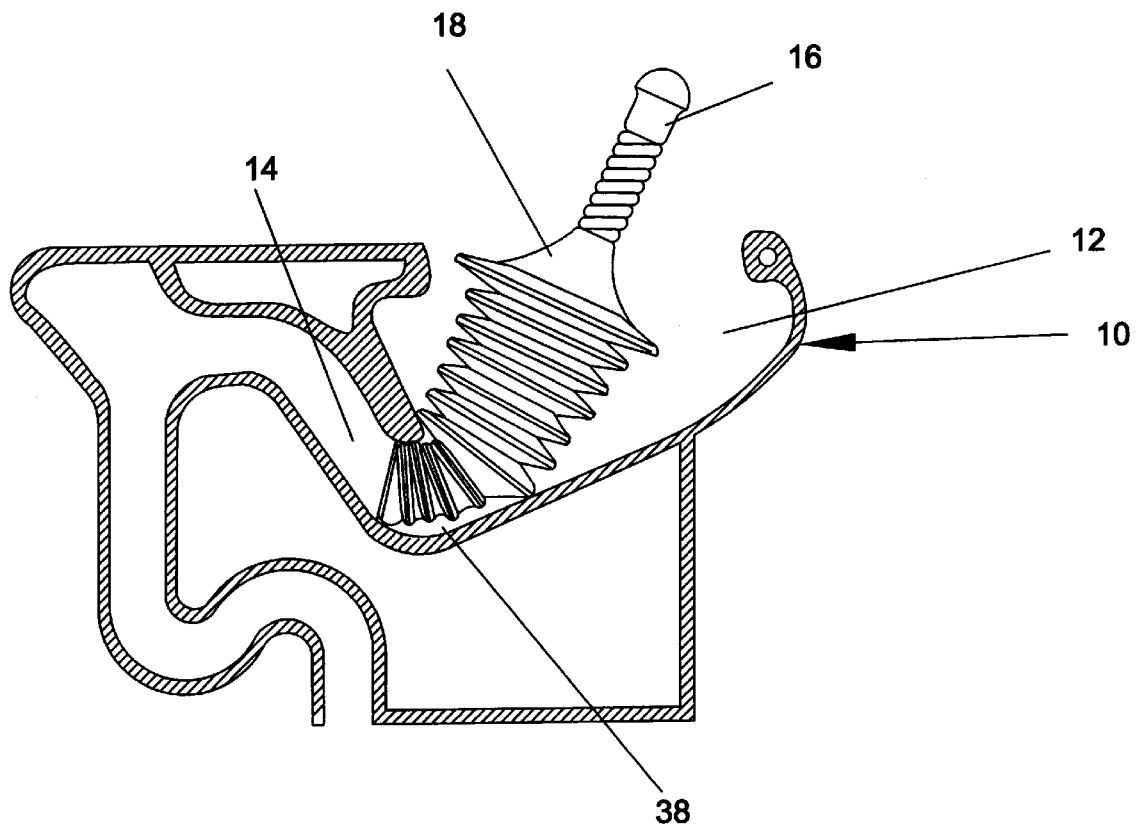
FIG. 1 is a cut away view of a 1.6 gallon toilet bowl with the plunger of the present invention in position to dislodge any obstructions in the throat.

The new 1.6 gallon toilets 10 have a bowl 12 which drains through a relatively narrow throat 14, as shown in FIG. 1. Conventional plungers are typically too wide to fit into the narrow throat and too rigid to seal against a vertically oriented throat or seal on the "lower" bowl of toilet bowls that are configured with a two-step upper and lower bowl section. Consequently, conventional plungers are unable to provide the appropriate pressure or suction for the purpose of dislodging any obstruction blocking the throat.

Figure 2A:
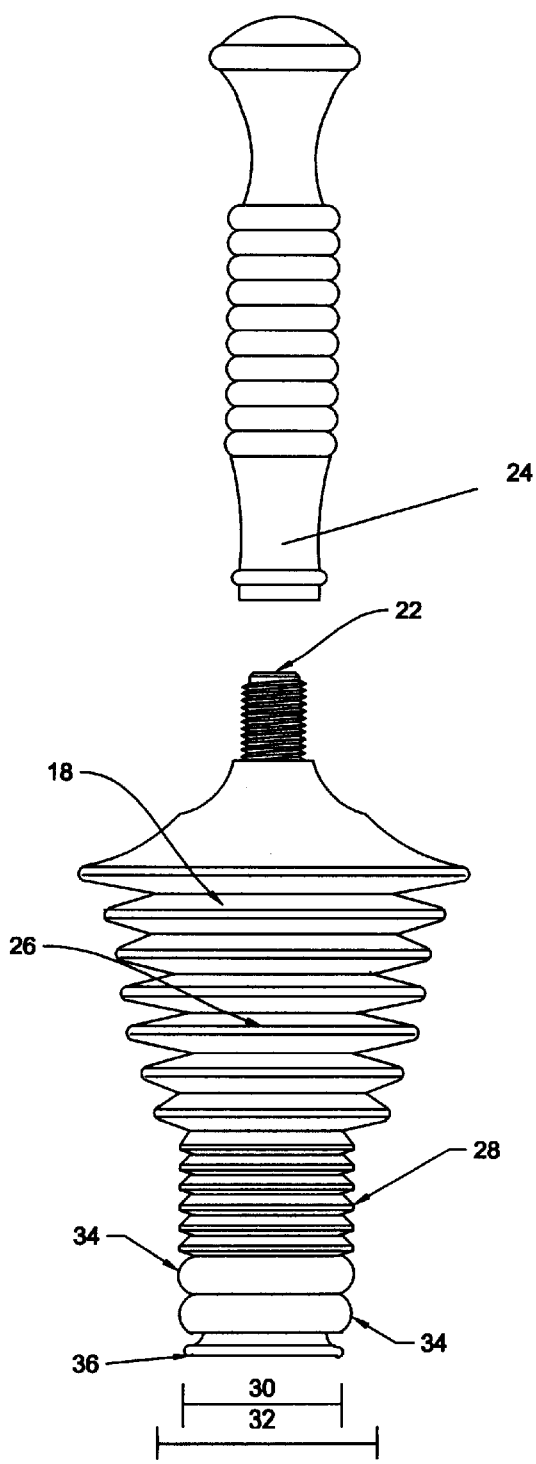
FIG. 2A is an exploded side view of the plunger of the present invention.
Figure 2B:
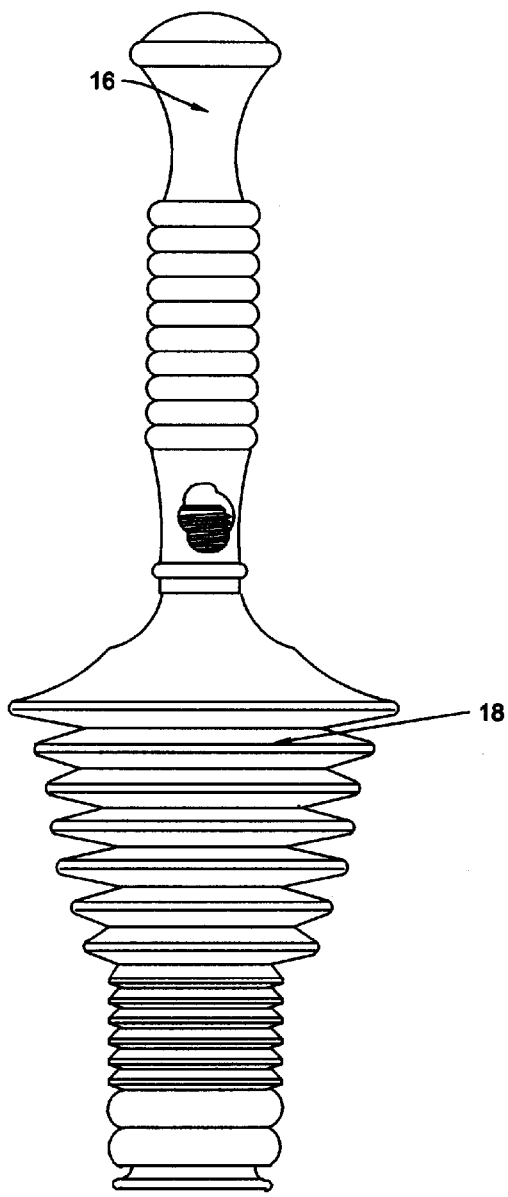
FIG. 2B is a side view of the plunger of the present invention.
Figure 3:
FIG. 3 is a perspective view of the plunger of the present invention.

The plunger of the present invention has a handle 16 and a head 18. (FIGS. 2A and 2B). The head is preferably made from flexible rubber or plastic material, preferably a blow molded material. The handle can be made from the same material as the head or may be made from other materials such as, for example, wood, ceramic or metal. The handle is preferably threadably connected to the head, but could be glued, snap-fit or integrally molded with the head. In the threaded embodiment, the head has a threaded stub extended from its rear end 22. The handle is preferably hollow at the end 24 and has threads formed on its inner surface. The threaded end of the handle is threaded onto the threads on the protruding stud 20 of the head 18.

The head portion is a pleated bellows consisting of two sections, a conically tapering section 26 and a constant diameter section 28. The conically tapering section has larger diameter at the rear end of the head and tapers down to a narrower diameter in a direction away from the rear end of the head. The bellows then continues into the constant diameter section in a direction way from the rear end and towards the front end of the head. The constant diameter section resembles an elephant-like trunk or nose. The constant diameter section of the bellows has a diameter 30 that is smaller than the diameter 32 of the bellows immediately adjacent to it. The constant diameter nose section is flexible due to the bellows design so it can readily follow the path of the throat and access vertical throats and other throats that are in hard to reach places. The forward portion of the head bellows is preferably stiffened by having two annular semicircular shell sections 34 abutting each other without forming a pleat between themselves. In this regard, the two annular sections would have a higher resistance to compressing against each other than the bellows. A narrower lip section 36 extends from the front end of the most forward annular semicircular shell toward the forward end of the head.

When inserted into the toilet bowl, the constant diameter section of the bellows head penetrates into the throat, while a forward end of the tapered section will seat over the outer perimeter of the mouth 38 of the throat (FIG. 1). The constant diameter or nose section of the head curves to follow the path of the throat as shown in FIG. 1. The stiffer forward portion of the nose follows the throat without compressing or jamming. As pressure is applied downward on the handle, the tapered section of the bellows compresses against the mouth 38 of the throat forming a seal. As a result, the water/air pressure generated by the compression of the bellows is directed through the nose section which is curved to follow the path of the throat. The water/air will be directed along the throat towards any obstruction therein. This effectively dislodges the obstruction, since the nose section of the plunger is directed along the axis of the throat. This is more effective at declogging the throat than plungers which direct the water/air off-axis in relation to the throat and obstruction. For example, a conventional plunger would direct the water/air towards the bottom of the toilet bowl rather than along the throat.

The toilet plunger embodied in the present invention has many advantages. Since the constant diameter section of the plunger head is small enough to fit into the throat, and the forward end of the tapered section of the plunger head seats against the outside perimeter of the throat, the plunger of the present invention provides a superior seal of the throat. The superior seal of the present invention provides for great pressure in the waste drain passage or throat to most effectively dislodge an object clogging it. Furthermore, the graduated, funnel nose, flexible bellows design of the plunger allows it to be effectively used with all types of toilets. This is even true for toilets wherein the drain hole is recessed and hence not readily accessible to common toilet plungers. Additionally, the graduated funnel nose design's flexibility also allows it to seal the throat of a toilet even when the throat is positioned vertically in relation to the toilet bowl. Since the head of this invention's toilet plunger has a smaller displacement than the typical cup-shaped toilet plunger head, unwanted spillage is also minimized. Furthermore, the bellows design wherein the pleats easily and smoothly compress during plunger use avoids sudden air surging characteristics of conventional toilet drain plungers, thereby also minimizing splash-back problems.

While the invention has been described in detail by specific reference to preferred embodiments thereof, it is understood that variations and modifications thereof may be made without departing from the true spirit and scope of the invention. For example, this invention could also be employed for use with sink or other types of drains.

Wherefore, having thus described the present invention, what is claimed is:

1. A plunger comprising:
   a handle, and
   a head comprising a pleated bellows and an elongated front section that is capable of interfacing with the throat of a toilet, wherein the elongated front section has a distal opening an exhibits a degree of flexibility and is of sufficient length to allow the front elongated section to bend with the shape of the throat while being inserted into the throat of the toilet to a point where the distal opening of the front section is directed parallel to the path of the throat such that water and air expelled from the distal opening of the front section is directed parallel to the path of the throat.

2. The plunger of claim 1 wherein the head is flexible.

3. The plunger of claim 1 wherein the elongated front section of the head has a constant average diameter.

4. The plunger of claim 1 wherein the elongated front section of the head is capable of creating a jam-fit within the throat of a toilet.

5. The plunger of claim 1 wherein the elongated front section is flexible enough to allow access to hard to reach toilet throats.

6. The plunger of claim 1 wherein the elongated front section is flexible enough to allow access to vertically-oriented toilet throat mouths.

7. A plunger comprising:

a handle; and a head comprising a first section connected to said handle and comprising a pleated bellows and a second section extending from the first section which is sized to interface with the throat of a toilet, wherein the second section has a distal opening and exhibits a degree of flexibility and Is of sufficient length to allow the elongated second section to bend with the share of the throat while being Inserted into the throat of the toilet to a point where the distal opening of the second section is directed parallel to the path of the throat such that water and air expelled from the distal opening of the second section is directed parallel to the path of the throat.

8. The plunger of claim 7 wherein:

the first section of the head has a larger diameter at the rear of the head and tapers down to a narrower diameter in a direction away from the rear end of the head.

9. The plunger of claim 8 wherein the second section of the head has a diameter smaller than the diameter of the bellows immediately adjacent to it.

10. The plunger of claim 9 wherein the first section of the head is engageable with the perimeter of a throat of a toilet, and wherein the second section of the head is insertable within said throat of a toilet.

11. The plunger of claim 7 wherein said second section has a constant average diameter.

12. The plunger of claim 7 wherein said second section has a pleated structure so as to be flexible and allow said second section to bend.

13. The plunger of claim 7 wherein the second section of the head further comprises two annular semi-circular shell sections abutting each other at the distal end of the second section for interfacing with a throat of a toilet.

14. The plunger of claim 7 further comprising a narrow lip section comprising the end of the distal end of the second section.

15. The plunger of claim 7 wherein the head portion is made of flexible, resilient plastic.

16. The plunger of claim 7 wherein the head is flexible enough to allow access to vertically-oriented toilet throat mouths.

17. The plunger of claim 7 wherein the head is flexible enough to allow access to hard to reach toilet throats.

18. The plunger of claim 7 wherein the handle is detachable from said head.

19. The plunger of claim 7 wherein said handle is integral with said head.

\* \* \* \* \*